United States Patent [19]

Sokol

[11] 4,234,475
[45] Nov. 18, 1980

[54] REACTING PROTEIN WITH ORGANIC ACID

[75] Inventor: Phillip E. Sokol, Rockville, Md.

[73] Assignee: The Gillette Company, Boston, Mass.

[21] Appl. No.: 605,166

[22] Filed: Aug. 15, 1975

[51] Int. Cl.$^3$ .............................................. C08H 1/06
[52] U.S. Cl. ................................ 260/112 R; 260/119; 260/123.5; 260/123.7
[58] Field of Search ................... 260/112 R, 117, 119, 260/121, 123, 123.5, 123.7

[56] References Cited

U.S. PATENT DOCUMENTS

| | | | |
|---|---|---|---|
| 2,164,284 | 6/1939 | Ralston | 260/112 R |
| 3,716,380 | 2/1973 | de la Potterie | 260/112 R |

OTHER PUBLICATIONS

Kirk-Othmer Encyclopedia of Chemical Technology, vol. 19, Interscience Pub., New York, 1969, p. 515.

Primary Examiner—Paul R. Michl
Attorney, Agent, or Firm—Richard A. Wise; Leonard J. Janowski

[57] ABSTRACT

Surface active agents are made by heating at 210° to 260° C. a mixture of a protein with an organic carboxylic acid at a ratio of one to ten equivalent weights of protein to one of acid. The mixture is preferably heated in an atmosphere of oxygen-free gas inert to the mixture. An inert solvent may be present.

4 Claims, No Drawings

REACTING PROTEIN WITH ORGANIC ACID

This invention relates to a process for preparing surface active agents directly from proteins by heating a mixture of the protein with a reagent which is an organic acid at 210° to 260° C., preferably at 220° to 240° C.

Protein-derived surface active agents are known for their mildness, biodegradability, resistance to liming, good protective-colloid and emulsifying properties, and softening effects of fabrics. These qualities recommend their use in cosmetics and other applications where contact with the skin occurs.

It has previously been proposed to prepare surface active agents by hydrolyzing proteinaceous materials followed by reacting a fatty acid halide or anhydride or a salt of such fatty acid with the hydrolysis product. (Stevens, C.E., in "Kirk-Othmer Encyclopedia of Chemical Technology," Vol. 19, Interscience Publishers, New York, N.Y., 1969, p. 515.) These multi-stage processes are complex and expensive to carry out, and in addition, when an acid halide or salt is employed, the product contains impurities such as halogen or metal atoms which is some cases may be undesirable.

It has also been proposed to react proteinaceous by-products of the meat packing industry directly with fatty acids or fats under distillation conditions to yield on oily condensate containing aliphatic nitriles and useful in insecticidal compositions or as solvents (Anderson et al. U.S. Pat. No. 2,164,284).

The present invention provides surface active agents from proteinaceous materials by a simple one-step operation without the necessity for isolation of intermediate products or of purification by removal of by-products.

The proteins or proteinaceous materials used in the process of the present invention may be from any conventional source; for example, there may be used waste products such as animal hides or hair and trimmings, bristles such as hog bristles, hoofs, feathers, e.g., chicken feathers, vegatable proteins such as soy or corn protein, fish scraps, or the like; more highly refined proteins such as collagen, elastin, casein, etc. may also be employed.

The organic acids which can be used include both aromatic acids and aliphatic carboxylic acids, the latter being preferred. Among the aromatic acids which can be used are benzoic, phthalic, toluic, xylic, cumic, p-tert-butyl benzoic, o-chlorobenzoic acid, p-bromobenzoic acid, 4-chlorophthalic acid, 3-bromophthalic acid, 1-naphthoic acid, 2-naphthoic acid, p-phenylbenzoic acid, diphenic acid, p-benzoylbenzoic acid and other similar aromatic mono- and polycarboxylic acids, both halogenated and unhalogenated and containing from 0 to 2 alkyl groups each having from 1 to 6 carbon atoms. Among the aliphatic acids are included both mono- and polybasic saturated aliphatic straight or branched chain carboxylic acids containing from 6 to 54 carbon atoms. Suitable aliphatic acids include caproic, caprylic, pelargonic, undecylenic, lauric, linoleic, linolenic, stearic, adipic, pimelic, azelaic, sebacic, "dimer acid", "trimer acid", and mixtures of any two or more of the foregoing. "Dimer acid" is an aliphatic dicarboxylic acid containing 36 carbon atoms made by polymerization of unsaturated $C_{18}$ fatty acids; "trimer acid" is an aliphatic tricarboxylic acid containing 54 carbon atoms also made by polymerization of unsaturated $C_{18}$ fatty acids.

The relative proportion of protein and of acid employed in the process of the present invention may be varied over a wide range. In general, the amount of protein may range from about 1 to about 10 equivalent weights for each equivalent weight of acid. The equivalent weight of a naturally occurring protein is assumed to be 120 for the purpose of this invention (i.e., the formula weight of an average amino acid unit in such proteins is about 120). The equivalent weight of the acid is its average formula weight divided by the number of carboxylic acid groups in the formula.

The processes are carried out either by preheating the fatty acid to the desired temperature within the range of 210°–260° C. (preferably 220°–240° C.), then mixing in the protein, or by mixing the protein with the fatty acid at lower temperatures, e.g., at room temperature or higher, then heating the mixture to the reaction temperature of 210°–260° C. (preferably 220°–240° C.). While an inert solvent may be used for the reaction, there is no particular advantage in doing so. The heating is continued until all of the large solid pieces or lumps of protein have dispersed in the liquid mass, whereupon the reaction is complete and the mixture can be allowed to cool. To achieve this result, it is usually necessary to continue the heating for about one hour at 240° C., or somewhat longer at lower temperatures.

When the heating is carried out in an atmosphere of air, some darkening and discoloration of the product occurs, and the product has some odor. While for many uses of the product, e.g., as an industrial surface active agent, such discoloration is not objectionable, it is desired in other cases, e.g., in the case of a product to be used in a cosmetic composition, to have a product as free as possible from dark color and from odor. Such products of higher purity can be obtained by carrying out the heating of the mixture in an atmosphere of nitrogen or other oxygen-free gas inert to the reactants. The process can be carried out at atmospheric pressure, and there is no advantage in carrying it out at a different pressure except when the acid is volatile, in which case the process should be carried out in a closed container or at elevated pressure to avoid evaporation and loss of the volatile ingredient. Heating at higher temperatures or for longer times than required to ensure completion of the reaction is unnecessary and tends to produce a deeper color and stronger odor in the product.

The molecular weight of the product, which is believed to consist of acid-terminated fragments or moieties of the original protein molecules, may vary depending upon the relative proportions of ingredients employed. However, regardless of the proportions used within the ranges set forth above, or the specific acid used in combination with any particular protein, the important properties of the products are much the same, all being useful as surface active agents. The residual protein amide linkages in the product are believed to provide complexing capability, making the products useful as surface active agents in hard water without the formation of insoluble salts of the products.

The products in general are partly soluble (to the extent of at least 80% by weight) in aqueous alkaline solutions, and also in polar organic solvents.

The following examples are intended to illustrate more clearly the nature of the invention without acting as a limitation upon its scope.

EXAMPLES 1-9

Various acids were heated at 180°-190° C. in an air atmosphere as set forth in the following table. In each case, the protein or proteinaceous material in dry solid form was then stirred slowly into the molten mass and stirring was continued while the mass was heated to 225°-250° C.; stirring was continued at the reaction temperature until all of the lumps or visible solid pieces of protein had dispersed in the mass, as set forth in Table I.

In each case the reaction was carried out with the mixture in contact with air, and in each case the product was a dark brown colored mass which solidified upon cooling to room temperature.

The solubility of each product was determined by reducing it to a finely-divided powder then stirring a known weight into a known quantity of aqueous ammonia (2%) at 20° C., then filtering and weighing the insoluble residue.

In each case a dilute solution of the product in aqueous ammonia was prepared, the solids were removed by filtration, and the surface tension of the solution was measured as well as the volume (in ml.) of stable foam which formed when 5.0 ml. of the solution was shaken in a 10 ml. cylinder. These properties and characteristics of the products are summarized in Table II.

TABLE I

| Example | Protein | Fatty Acid | Equivalents Ratio of Protein Acid | % Solubility in Aqueous $NH_4CH$ |
|---|---|---|---|---|
| 1 | Chicken feathers | lauric | 5:1 | 86 |
| 2 | Chicken feathers | lauric | 2:1 | 75 |
| 3 | Vegetable soy protein | lauric | 2:1 | 83 |
| 4 | Edible gelatin (animal glue) | lauric | 2:1 | 84 |
| 5 | Edible gelatin (animal glue) | lauric | 9:1 | 95 |
| 6 | Edible gelatin (animal glue) | lauric | 3:1 | 70 |
| 7 | Chicken feathers | undecylenic | 5:1 | 92 |
| 8 | Edible gelatin (animal glue) | lauric | 5:1 | 81 |
| 9 | Edible gelatin (animal glue) | stearic | 2:1 | 22 |

TABLE II

| Example | Conc. of Solution in % Solids | Surface Tension in dynes/cm. | Foaming in ml. |
|---|---|---|---|
| 1 | 0.86 | 34.2 | 0 |
| 2 | 1.20 | 29.2 | 8.0 |
|   | 0.12 | 32.9 | 2.3 |
| 3 | 0.05 | 29.0 | 2.3 |
| 4 | 0.26 | 31.9 | 4.2 |
|   | 0.32 | 27.3 | 4.2 |
| 5 | 0.9 | 31.3 | 4.3 |
|   | 0.09 | 34.3 | 1.4 |
| 6 | 0.22 | 30.6 | 3.0 |
| 7 | 0.33 | 39.6 | 3.0 |
| 8 | 0.21 | 30.5 | 3.0 |
| 9 | 0.13 | 46.5 | 0 |

Similar products can be prepared by using as the acid in the process described above p-tert-butylbenzoic acid or dimer acid with hog bristle at a protein:acid ratio of 3:1, or dimer acid at a ratio of 6:1 with hog bristle, the product in each case being 100% soluble in aqueous ammonia.

The surface tension and foaming characteristics of the solutions are in general comparable with those of commercially available surface active agents. The products are also found to be at least partially soluble in acetone, chloroform, and ethanol; some are completely soluble. On the basis of a variety of analyses, it is believed that the process involves a thermal condensation reaction in which terminal carboxylate groups are produced by a transamidification reaction.

What is claimed is:

1. The method of making a surface active agent which comprises heating at a temperature from 210° but not exceeding 260° C., a mixture of one to ten equivalent weights of a protein with one equivalent weight of a reagent which is a member of the group consisting of aromatic carboxylic acids, alkylated aromatic carboxylic acids in which each alkyl group has from 1 to 6 carbon atoms, halogenated aromatic carboxylic acids, and saturated and unsaturated aliphatic carboxylic acids having from 6 to 54 carbon atoms.

2. The method as claimed in claim 1 in which the reagent is an aliphatic saturated or unsaturated carboxylic acid having from 6 to 54 carbon atoms.

3. The method as claimed in claim 1 in which the heating is carried out at 220° to 240° C.

4. The method as claimed in claim 1 in which the mixture is maintained during the heating step in an atmosphere of oxygen-free gas inert to the mixture.

* * * * *

UNITED STATES PATENT AND TRADEMARK OFFICE
CERTIFICATE OF CORRECTION

PATENT NO. : 4,234,475
DATED : November 18, 1980
INVENTOR(S) : Phillip E. Sokol

It is certified that error appears in the above-identified patent and that said Letters Patent are hereby corrected as shown below:

Column 1, line 58, after "saturated" insert -- and unsaturated --.

Signed and Sealed this

Twenty-sixth Day of May 1981

[SEAL]

Attest:

RENE D. TEGTMEYER

*Attesting Officer*     *Acting Commissioner of Patents and Trademarks*